(12) United States Patent
Robey

(10) Patent No.: US 6,620,940 B1
(45) Date of Patent: Sep. 16, 2003

(54) PALLADIUM-CATALYZED CROSS-COUPLING CHEMISTRY ON 3-CHLORO-4-HALO-1,2,5-THIADIAZOLE

(75) Inventor: Roger Lewis Robey, Greenwood, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 09/671,854

(22) Filed: Sep. 27, 2000

Related U.S. Application Data

(62) Division of application No. 09/370,957, filed on Aug. 10, 1999, now abandoned.
(60) Provisional application No. 60/097,424, filed on Aug. 20, 1998.

(51) Int. Cl.[7] ............................................. C07D 285/10
(52) U.S. Cl. ...................................................... 548/134
(58) Field of Search ......................................... 548/134

(56) References Cited

U.S. PATENT DOCUMENTS

| | | | | |
|---|---|---|---|---|
| 3,419,572 A | * | 12/1968 | Weinstock et al. | ........... 260/302 |
| 5,332,825 A | | 7/1994 | Buckland | ..................... 546/330 |
| 5,646,289 A | | 7/1997 | Alt et al. | ..................... 548/110 |
| 5,766,833 A | | 6/1998 | Suematsu et al. | ........... 430/489 |

OTHER PUBLICATIONS

Weinstock et al.; *Journ. Org. Chem.*, vol. 32, p. 2823 (1967); A General Synthetic System for 1,2,5–Thiadiazoles.

* cited by examiner

*Primary Examiner*—Laura L. Stockton
(74) *Attorney, Agent, or Firm*—David M. Stemerick; Arleen Palmberg

(57) ABSTRACT

The present invention relates to 3-chloro-4-halo-1,2,5-thiadiazole compounds, a method of producing novel mono- and di-substituted-1,2,5-thiadiazoles therefrom, as well as mono- and di-substituted -1,2,5-thiadiazoles.

1 Claim, No Drawings

PALLADIUM-CATALYZED CROSS-COUPLING CHEMISTRY ON 3-CHLORO-4-HALO-1,2,5-THIADIAZOLE

CROSS REFERENCE

The present application is a divisional of U.S. application Ser. No. 09/370,957 filed Aug. 10, 1999, now abandoned which claims the benefit of provisional application Serial No. 60/097,424, filed Aug. 20, 1998.

BACKGROUND OF THE INVENTION

The present invention relates to 3-chloro-4-halo-1,2,5-thiadiazole compounds and a method of producing novel mono- and di-substituted-1,2,5-thiadiazoles therefrom.

Since the discovery of 2,1,3-benzothiadiazole by Hinsberg in 1889 [1], chemists have shown an increasing interest in the chemistry of 1,2,5-thiadiazoles and 1,2,5-selenadiazoles.

Various compounds comprising a heteroaromatic ring of the 1,2,5-thiadiazole type present interesting properties in the pharmaceutical or agrochemical industry, and in the field of polymers. Thus, several molecules have been shown to have antibiotic [2], antihistamine [3], β-adrenergic [4] and anticholingergic activities [5], as well as inhibitory activities on HIV-1 transcriptase [6]. Other thiadiazoles are active as a fungicide [7], bactericide [8], herbicide [9], growth regulator [10], insecticide [11], coccidiostatic agent [12] or antihelmetic agent [13]. Finally, the 1,2,5-thiadiazole ring has also been incorporated in several polymers presenting, among other properties, high thermal and chemical stabilities [14].

The various syntheses of 1,2,5-thiadiazoles, largely developed during the '60s, can be grouped as a function of the precursor fragments used to construct the thiadiazole ring. The following approaches have been developed:

- cyclization of an N—C—C—N fragment by a derivative S: [4+1] approach
- cyclization of a C—C fragment with a derivative N—S—N: [3+2] approach (type A), and
- cyclization of a C—C—N fragment by a derivative S—N: [3+2] approach (type B).

The [4+1] approaches use the cyclization with sodium mono- or dichloride of compounds of the following types: α-aminoacetonitrile, α-dioxime, α-diamine, αaminoamide, α-cyanoimidate and α-cyanoamide. This approach was largely developed by Weinstock [15] during the 1950s.

α-aminoacetonitriles are prepared from aldehydes via a Strecker reaction:

(eq 1)

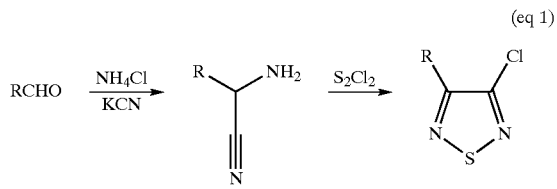

α-dioximes, prepared from 1,2-diketone precursors and α-diamines lead to dialkyl- and diarylthiadiazoles:

(eq 2)

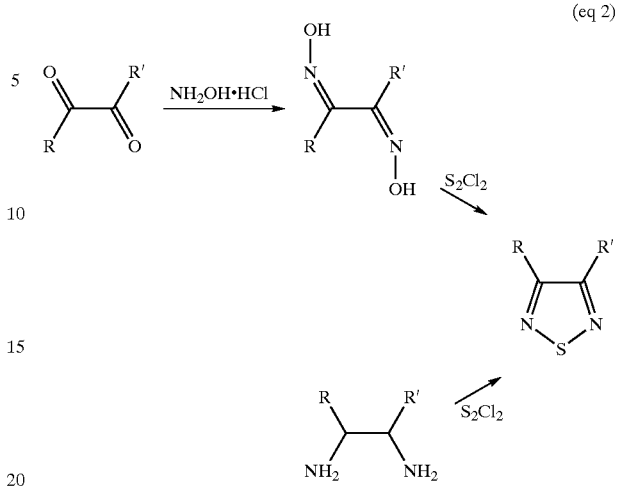

α-aminoamides, derived from amino acids, lead to hydroxylated thiadiazoles, which can be converted to halogenated thiadiazoles by treatment with phosphorus oxychloride or oxybromide [16]

(eq 3)

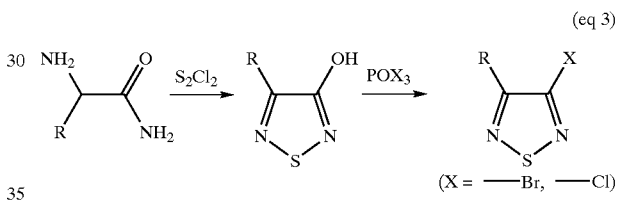

(X = —Br, —Cl)

Cyanogen, the precursor of α-cyanoamides and α-cyanoimidates, allows the production of 3-chloro-4-hydroxylated, 3-chloro-4-alkoxylated and 3,4-dichlorinated derivatives.

(eq 4)

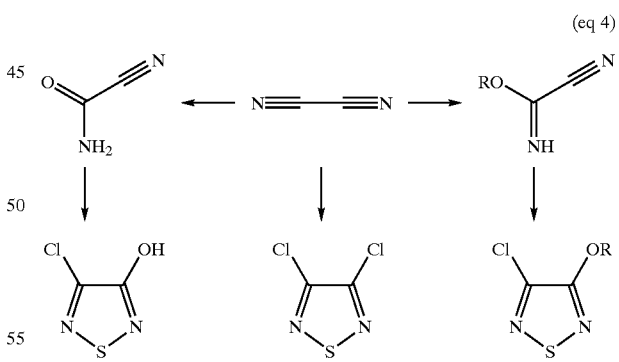

The syntheses of type [3+2] can be divided into two subclasses depending on whether the carbon fragment is of the C—C—N or C—C type. The first subclass ([3+2] type B) involves primarily the reaction of benzyl ketones, the corresponding oximes or the α,α-diahalogenoketoximes with derivatives of the sulfur diimide or tetranitride type in the cyclization step. Such an approach was applied to the preparation of numerous 3-chloro- and 3-bromo-4-aryl-1,2,5-thiadiazoles with excellent yields [17].

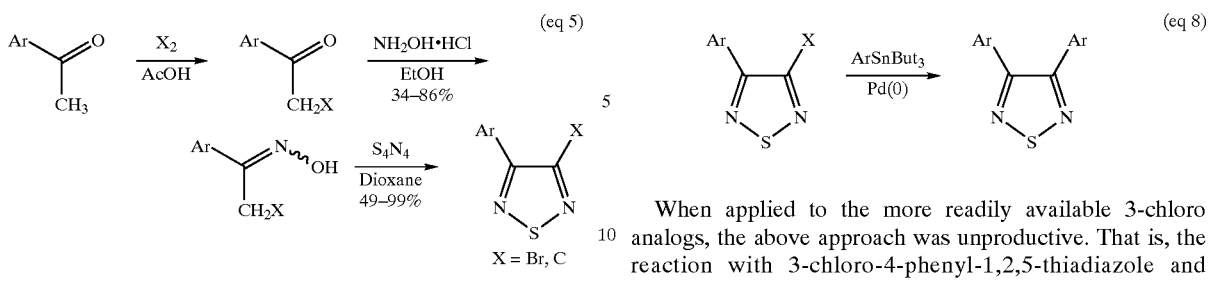

(eq 5)

The second subclass ([3+2] type A) primarily uses disubstituted acetylene derivatives, as shown below (eq. 6):

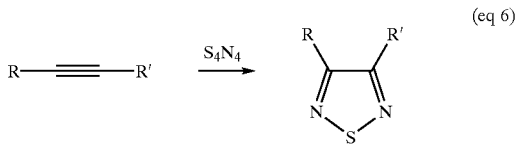

(eq 6)

where R and R' are aryl, alkyl, $CO_2R$ or CN.

Unfortunately, all of the standard methods for construction of the 1,2,5-thiadiazole ring have various drawbacks when applied to large-scale syntheses, including:
- unavailability of cyanogen and certain other precursors,
- lengthy syntheses often leading to modest overall yields,
- use of very toxic, corrosive and sometimes explosive reagents (for example: $S_4N_4$ [18]), and
- production of sulfur or its derivatives in the cyclization step, making purification difficult.

Alternate synthetic pathways, which are more general and allow the production of 3-chloro-4-alkyl- and 3-chloro-4-arylthiadiazoles, are therefore desirable. One of the fundamental methods of creating a carbon-carbon bond between a halogenated heterocycle and an aliphatic or aromatic group is the coupling reaction catalyzed by transition metals, as illustrated below:

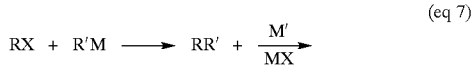

(eq 7)

where R and R' are aryl, alkenyl, alkynyl, or alkyl; M is Li, Mg, Zn, Cu, Al, Si, Sn, or B and M' is Pd or Ni. The application of transition metal chemistry for the production of various heterocyclic ring systems is known.

In 1972, Kumada [19] and Corriu [20] independently reported that the reaction between Grignard reagents and alkyl or aryl halides can be effectively catalyzed by nickel complexes. Murahashi [21] later published the first example of catalysis with palladium using the same reaction. Extraordinary advances in the field of coupling reactions catalyzed by transition metals followed with the use of derivatives of zinc, aluminum and zirconium [22], lithium [23], copper [24], silicon [25], tin [26] and boron [27].

Palladium catalysis has been applied to form numerous π-deficient heterocycles such as pyridine, pyrimidine and pyrazines [28]. However, palladium catalysis infrequently has been applied to other heterocyclic systems, including 1,2,5-thiadiazoles. A few recent publications reported the synthesis of 3,4-diaryl-1,2,5-thiadiazoles by reacting 3-bromo- or 3-trifluoromethanesulfonyl-4-aryl-1,2,5-thiadiazoles and arylstannanes ([29], JP 10025284 A2 980127, and JP 05163258 A2 930629).

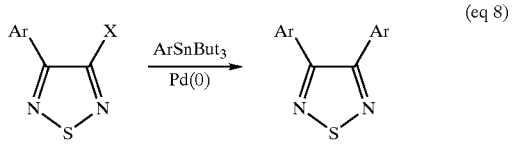

(eq 8)

When applied to the more readily available 3-chloro analogs, the above approach was unproductive. That is, the reaction with 3-chloro-4-phenyl-1,2,5-thiadiazole and tributyl(4-chlorophenyl)stannane led to the diarylated derivative with a yield of only 37%.

Thus, despite these recent advances, novel methods of producing 1,2,5-thiadiazoles with broader applicability for various substituents are desirable.

BRIEF SUMMARY OF THE INVENTION

The present invention provides a method of synthesizing 3-chloro-4-substituted derivatives by reacting 3-chloro-4-halo-1,2,5-thiadiazoles with an organostannane or organoborane in the presence of a catalytic amount of palladium (eq 9):

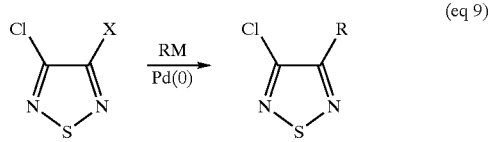

(eq 9)

where X is chloro, bromo, or iodo; and

RM is an organometallic group such as an organostannane or an organoborane (where R is an alkyl, alkenyl, alkynyl, aryl, or heteroaromatic group)

The present invention also provides a method of synthesizing novel 3,4-disubstituted-1,2,5-thiadiazoles from previously unknown 3-chloro-4-substituted-1,2,5-thiadiazoles by a further palladium-catalyzed cross-coupling reaction (eq 10):

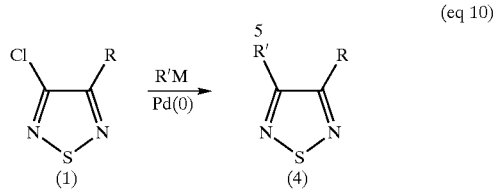

(eq 10)

where R is as defined above; and

R'M is an organometallic group such as an organostannane or an organoborane (where R' is an alkyl, alkynyl, vinyl, allyl, aryl, or heteroaromatic group or is $-OR^5$, $-SR^5$ or $-NR^5R^6$)

In the above formulae, R and R' may be unsubstituted or substituted one to three times with a substituent selected from the group consisting of alkyl, alkenyls, alkynyls, halogen, hydroxy, oxo, phosphoryl, thiol, sulfinyl, sulfonyl, aryl, heterocyclic, amine, imine, nitro, cyano, amidino, carbonyl; wherein the moieties substituted on the hydrocarbon chain can themselves be substituted with one to three further substituents.

The present invention provides novel 3-chloro-4-substituted-1,2,5-thiadiazoles of the formula (1):

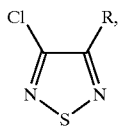

(1)

where R is —CR$^1$=CR$^2$R$^3$ or —C≡CR$^4$;

R$^1$ is hydrogen, alkyl, —OR$^5$, —SR$^5$ or —NR$^5$R$^6$;

R$^2$ and R$^3$ are each, independently, hydrogen, fluorine, alkyl, nitriles, O-protected alcohols, S-protected thiol, N-protected amine, CO-protected aldehydes, esters, alkylaryl and phosphine, R$^4$ is alkyl, aryl, or a C-protecting group (such as trimethylsilyl (TMS) or t-butyl-dimethylsilyl (TBS)); and R$^5$ and R$^6$ are each, independently, a protecting group, alkyl, alkenyl, alkynyl, aryl, heterocyclic or heteroaromatic group or where R$^5$ and R$^6$ together with the N which they substitute, form a heteroaromatic or heteroaromatic group.

The present invention also provides novel thiadiazole compounds of the formula:

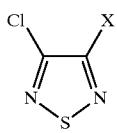

where X is iodo (2) or bromo (3).

DETAILED DESCRIPTION OF THE INVENTION

Definitions

"Alcohols" include groups of the formula —OH and —OP, where P is a O-protecting group such as Boc.

"Aldehydes" include groups of the formula —C(=O)H.

"Alkenyl" means a substituted or unsubstituted, straight or branched, unsaturated hydrocarbon chain that contains at least one double bond and 2 to 20, preferably 2 to 6, carbon atoms. Allyl groups, —CH$_2$CH=CH$_2$, and vinyl groups, —CH=CH$_2$, are exemplary alkenyl groups.

"Alkoxy" means an —O-alkyl group such as methoxy, ethoxy, n-propoxy, isopropoxy, n-butoxy, t-butoxy, etc.

"Alkyl" means a substituted or unsubstituted, straight, branched or cyclic saturated hydrocarbon chain that contains 1 to 20, preferably 1 to 6, carbon atoms. Examples include methyl, ethyl, propyl, isopropyl, butyl, isobutyl, pentyl, hexyl, cyclopropyl, cyclobutyl, cyclopentyl and cyclohexyl.

"Alkylaryl" means a C$_{1-4}$ alkyl group bearing one or more aryl groups. Representatives of this group include benzyl, o-nitrobenzyl, p-nitrobenzyl, p-halobenzyl (such as p-chlorobenzyl, p-bromobenzyl, p-iodobenzyl), 1-phenylethyl, 2-phenylethyl, 3-phenylpropyl, 4-phenylbutyl, 2-methyl-2-phenylpropyl, (2,6-dichlorophenyl)methyl, bis(2,6-dichlorophenyl)methyl, (4-hydroxyphenyl)methyl, (2,4-dinitrophenyl)methyl, diphenylmethyl, triphenylmethyl, (p-methoxyphenyl)-diphenylmethyl, bis(p-methoxyphenyl)methyl, bis(2-nitrophenyl)methyl, and the like. "Alkynyl" means a substituted or unsubstituted, straight or branched, unsaturated hydrocarbon that contains at least one triple bond and 2 to 20, preferably 2 to 6, carbon atoms.

"Amine" means a primary, secondary or tertiary amine. Suitable amines are of the formula —NH$_2$, —NHR, or —NR$_2$, where each R is independently an alkyl group. Exemplary amines include methylamine, dimethylamine, methylethylamine, isopropylamine, etc.

"Aryl" means or "aromatic" means a substituted or unsubstituted, mono- or bicyclic carbocyclic aromatic ring, preferably containing 6 to 10 carbon atoms. Examples include phenyl (Ph) or naphthyl.

"Esters" include groups of the formula —C(=O)OR, where R is an alkyl group. Exemplary groups include methyl ester, ethyl ester, etc.

"Halogen" means chlorine, bromine, iodine, or fluorine.

"Heteroaromatic" means a 5–10 membered, substituted or unsubstituted mono-, bi- or tricyclic aromatic group wherein one or more members of the aromatic ring is a heteroatom, preferably oxygen, nitrogen or sulfur. Examples include benzofuran, benzothiophene, furan, imidazole, indole, isothiazole, oxazole, piperazine, pyrazine, pyrazole, pyridazine, pyridine, pyrimidine, pyrrole, quinoline, thiazole, and thiophene.

"Heterocyclic" means a 5–10 membered, substituted or unsubstituted cyclic hydrocarbon ring wherein one or more members of the ring is a heteroatom, preferably oxygen, nitrogen or sulfur. Examples include morpholino and piperazino.

"Imine" includes groups of the formula —C=N—H or —C=N—R, where R is alkyl.

"Nitriles" include groups of the formula —C≡N.

"Protecting group" means a group used to protect a heteroatom such as oxygen, nitrogen, sulfur or phosphorus from chemical reaction. For example, a O-protecting group is used to protect an oxygen heteroatom, such as in a hydroxy group, from reaction. Suitable O-protecting groups include t-butyl ether, benzyl ethers, etc. Protecting groups are well known in the art, see for example Greene, T. W. Protective Groups in Organic Synthesis, John Wiley and Sons, Inc: New York. 1991. Preferred protecting groups include, but are not limited to, the "Boc" protecting group, trialkyl silyl groups such as TBS (tert-butyldimethylsilyl, Si(CH$_3$)$_2$C(CH$_3$)$_3$), MEM, MOM, SEM, and THP.

"Substituted" means that the moiety contains at least one, preferably 1–3 substituent(s). These substituents can optionally be further substituted with 1–3 substituents. Examples of substituted substituents include carboxamide, alkylmercapto, alkylsulphonyl, alkylamino, dialkylamino, carboxylate, alkoxycarbonyl, alkylaryl, aralkyl, alkylheterocyclic ring, etc. Suitable substituents include hydrogen, hydroxyl, amino, oxy, carbonyl, thiol, alkyl, alkenyl, alkynyl, alkoxy, halo, nitrile, nitro, aryl and heterocyclic ring.

"Thiols" include compounds of the formula —SH or —SR where R is alkyl. Exemplary thiols include methanethiol, ethanethiol, propanethiol, etc.

Novel 3-Chloro-4-substituted-1,2,5-thiadiazoles of the Formula (1)

The present invention also provides novel 3-chloro-4-substituted-1,2,5-thiadiazoles of the formula (1):

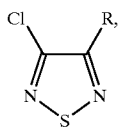

where R is as defined above.

Representative new compounds include:

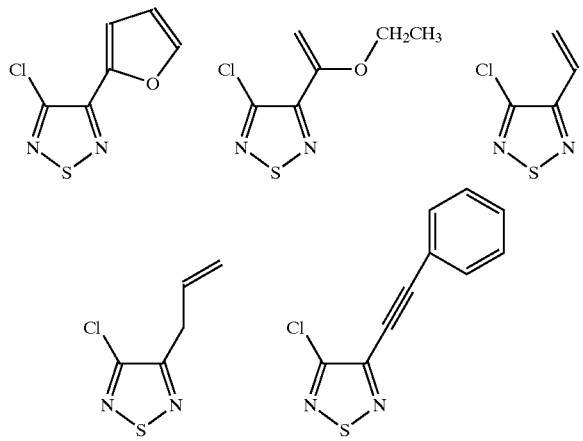

which are:

3-chloro-4-(furan-2-yl)-1,2,5-thiadiazole,
3-chloro-4-(1-ethoxyvinyl)-1,2,5-thiadiazole,
3-chloro-4-vinyl-1,2,5-thiadiazole,
3-chloro-4-allyl-1,2,5-thiadiazole, and
3-chloro-4-phenylethynyl-1,2,5-thiadiazole, respectively.

Novel compounds of the formula (1) can be prepared from 3-chloro-4-(chloro-, bromo- or iodo-)-1,2,5-thiadiazoles as described below using palladium-catalyzed cross-coupling chemistry.

Novel 3,4-Disubstituted-1,2,5-thiadiazoles of the Formula (4)

The present invention also provides novel 3,4-disubstituted-1,2,5-thiadiazoles of the formula (4):

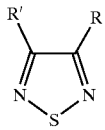

where R is as defined above; and

R' is alkyl, alkenyl, alkynyl, aryl or heteroaromatic or —$OR^9$, —$SR^9$, or —$NR^9R^{10}$, where $R^9$ and $R^{10}$ are each, independently, alkyl, alkenyl, alkynyl, aryl, heterocyclic or heteroaromatic group or where $R^9$ and $R^{10}$ together with the N which they substitute, form a heterocyclic or heteroaromatic group.

When R' is alkenyl, alkynyl, aryl or heteroaromatic, compounds of the formula (4) can be formed from 3-chloro-4-substituted-1,2,5-thiadiazoles (1) and an organostannane or an organoborane in a second palladium catalyzed cross-coupling reaction under the conditions described above (see also JP 10025284 A2 980127 and JP 05163258 A2 930629). It is possible to first hydrolyze the 3-chloro group to a 3-hydroxy derivative (Robey & Ward, PCT Publication No. WO96/3843 1) and subsequently brominate the same (Hanasaki, Heterocycles, 1996, 43(11): 2435) to form a 3-bromo-4-substituted-1,2,5-thiadiazoles (see eq 11 below). This intermediate is more reactive to palladium catalyzed cross-coupling than the 3-chloro derivative.

When R' is alkyl, compounds of the formula (4) can be formed from 3-chloro-, 3-bromo-, or 3-iodo-4-substituted-1,2,5-thiadiazoles and an organostannane or an organoborane in a second palladium catalyzed cross-coupling reaction under the conditions described above. 3-bromo-4-substituted-1,2,5-thiadiazoles is preferably used. 3-bromo-4-substituted-1,2,5-thiadiazoles can be formed from 3-chloro-4-substituted-1,2,5-thiadiazoles by hydrolysis to the 3-hydroxy-derivative and subsequent bromination. The overall reaction is shown below (eq 11):

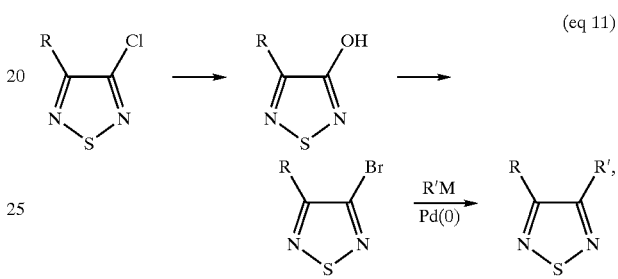

(eq 11)

where M is, for example, —$B(OH)_2$, —$BEt_2$, —$SnBu_3$.

When R' is —$OR^9$, —$SR^9$, or —$NR^9R^{10}$, compounds of the formula (4) can be formed from 3-chloro-4-substituted-1,2,5-thiadiazoles (1) by using all conventional methods reported in the literature. Alternatively, when R' is —$OR^9$, —$SR^9$, or —$NR^9R^{10}$, the R' group can be first introduced using methods known in the art and R can subsequently be added via a cross-coupling reaction as described above (eq 12):

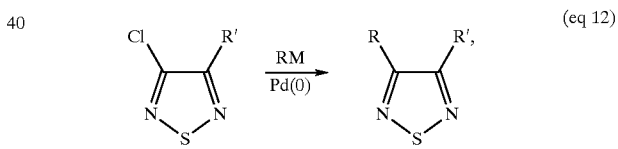

(eq 12)

It should be understood that when R' is introduced first, if R is alkyl, then it is preferable to hydrolyze the chlorine, brominate, and then conduct the cross-coupling as shown above in eq (11).

Novel 3-Chloro-4-halo-1,2,5-thiadiazoles of the Formulae (2) and (3)

Novel compounds of the formula:

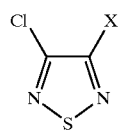

where X is iodo (2) or bromo (3) can be prepared by reacting an alkyl nitrite, copper(I)halide or copper(II) halide, and 3-amino-4-chloro-1,2,5-thiadiazole (5) in solution, using the methods described by Doyle et al., J. Org. Chem., vol. 42, p. 2426, 1977.

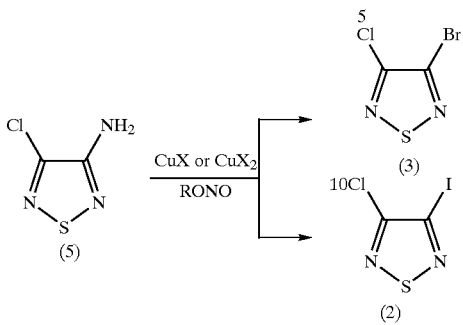

The 3-amino-4-chloro-1,2,5-thiadiazole has been previously prepared in 44% overall yield as described by Weinstock et al., J. Org. Chem., 2823, 1967; Lentia, DE 1175683, 1962; and Oesterreich Stickstoffwerke, BE 629551, 1963.

Method of Producing 3-Chloro-4-substituted-1,2,5-thiadiazole (1) by Palladium Catalyzed Cross-coupling The method of the present invention involves coupling 3-chloro-4-halo-1,2,5-thiadiazole with an organometallic group in the presence of a palladium catalyst (eq 9):

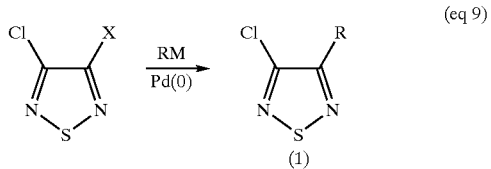

(eq 9)

where X is a halogen and RM is an organometallic complex where R is alkyl, alkynyl, vinyl, allyl, aryl, or heteroaromatic group.

Method using 3,4-Dichloro-1,2,5-thiadiazoles

In general, the organometallic complex and the palladium (0) catalyst are added to a solution of the 1,2,5-thiadiazole in solvent and are heated at reflux for 20–24 hours. The organometallic complex and the 1,2,5-thiadiazole are used in approximately equal molar ratio, preferably from about 1:1 to 1:0.95, respectively. A catalytic amount of palladium is used initially; however, further amounts of palladium(0) catalyst can optionally be added during the reaction.

Suitable solvents have boiling points greater than 100° C. and are either monophasic or diphasic. Preferred solvents include toluene, dioxane, dimethoxyethane (dme), water and mixtures thereof.

Suitable palladium(0) catalysts include any tetrasubstituted palladium(0) catalyst. Some of these palladium(0) catalysts are commercially available. Preferably, tetrakistriphenyl-phosphine palladium (0) ((PPh$_3$)$_4$Pd) is used.

Suitable organometallic compounds are organostannanes (such as described by Stille, Angew. Chem. Int. Ed. Eng., vol. 25, p. 508 (1986) [26]) and organoboranes (such as described by Miyaura & Suzuki, Chem. Rev., vol. 95, p. 2457, 1995 [27b]). When 3,4-dichloro-1,2,5-thiadiazole is used as starting material, organostannanes are preferably used.

Suitable organostannanes include RSn(alkyl)$_3$, such as RSnBut$_3$ and RSnMe$_3$, where R is as described above. RSnMe$_3$ is preferably used, as its by-products are soluble in water. However, many RSnBut$_3$ compounds are commercially available.

Suitable borane derivatives are described therein and include RB(OH)$_2$, RB(alkyl)$_2$ (such as RB(Et)$_2$) and RB(alkoxy)$_2$, where R is as described above. Most preferably, the borane has the general formula RB(OH)$_2$. When an organoborane is used, the reaction mixture further comprises a base, preferably an alkaline- or alkaline-earth metal base such as K$_2$CO$_3$, KF, CsF, Cs$_2$CO$_3$, Na$_2$CO$_3$. Due to the presence of the base, the solvent is preferably a bi-phasic organic/water mixture. However, a monophasic organic mixture can also be used if a phase-transfer catalyst is included.

Method using 3-Chloro-4-(iodo- or Bromo-)-1,2,5-thiadiazoles

In general, the organometallic complex and the palladium (0) catalyst are added to a solution of the 1,2,5-thiadiazole in solvent and are heated at reflux. When the halogen is bromine, the reaction is conducted for about 6–10 hours, preferably about 8 hours. When the halogen is iodine, the reaction is conducted for about 1–3 hours, preferably about 2 hours. Further amounts of palladium(0) catalyst are optionally added during the reaction. Suitable solvents have boiling points greater than 100° C. and are either monophasic or diphasic. Preferred solvents include toluene, dioxane, dimethoxyethane (dme), water and mixtures thereof.

Suitable palladium(0) catalysts include any palladium(0) species, including commercially available Pd(PPh$_3$)$_4$ and Pd$_2$(dba)$_3$ or can be prepared in situ be reduction of Pd(II) precursors like Pd(OAc)$_2$ or PdCl$_2$ in the presence of phosphine.

Suitable organometallic compounds are organostannanes and organoboranes. When 3-chloro-4-(iodo- or bromo-)-1,2,5-thiadiazoles are used as starting material, organoboranes are preferably used. The use of both organometallic complexes are described above. When organostannanes are used, the reaction is preferably run in a monophasic system (particularly toluene or dioxane). When organoboranes are used, the reaction is run in a biphasic mixture (such as toluene/water), using a base such as KF.

Method of Producing 3,4-Disubstituted-1,2,5-thiadiazole by Palladium Catalyzed Cross-coupling The present invention also includes a method of cross-coupling 3-chloro-4-substituted-1,2,5-thiadiazoles with an organometallic group in the presence of a palladium(0) catalyst (eq 13):

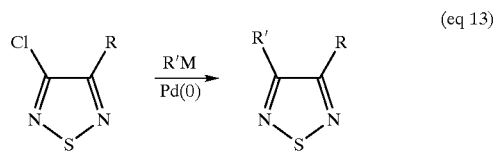

(eq 13)

where R and R' are each, independently, an alkyl, alkynyl, vinyl, allyl, aryl, or heteroaromatic group, or where R is an alkyl, alkynyl, vinyl, allyl, aryl, or heteroaromatic group and R' is —OR$^5$, —SR$^5$ or —NR$^5$R$^6$, (where R$^5$ and R$^6$ are as defined above).

As compared with previous methods (JP 10025284 and JP 05163258), the present method is more general and also makes it possible to use the much less toxic organoborane reagents. For example, when starting from 3-chloro-4-phenyl-1,2,5-thiadiazole, up to 80% yield was obtained in the synthesis of the 3,4-diphenyl-1,2,5-thiadiazole, with PhB(OH)$_2$ and KF as base.

EXAMPLES

Apparatuses

All the coupling reactions were carried out under a nitrogen or argon atmosphere in multiple-neck reactors allowing the addition of the reagents and the collection of samples without contacting the air.

The reactions were monitored by thin layer chromatography (silica plates, Merck 60 F$_{254}$) and by HPLC (Waters: $\lambda$=235 nm, eluant=CH$_3$CN/H$_2$O).

The nuclear magnetic resonance spectra were recorded using a Brucker 400 MHz spectrometer.

Reagents, Solvents and Catalysts

The 3,4-dichloro-1,2,5-thiadiazole (Degussa) was redistilled (155° C./760 mm).

The organostannanes (Aldrich, except for tributyl(3-pyridyl) (Maybridge)) were used as is.

The phenylboric acid (Acros) and the diethyl(3-pyridyl) borane (Aldrich) were used as is.

The toluene and the dioxane, of anhydrous grade under a film (Aldrich) were degassed with nitrogen before use.

The demineralized water was degassed.

The catalysts are commercial catalysts or they were prepared in situ from commercial precursors used without prior purification:
  tetrakis(triphenylphosphine)palladium(0) (Acros),
  dichlorobis(tricyclohexylphosphine)palladium(II) (Aldrich),
  bis(triphenylphosphine)dichloropalladium(II) (Fluka),
  bis(acetonitrile)dichloropalladium(II) (Aldrich)
  [1,2-bis(diphenylphosphino)ethane]dichloropalladium (II) (Aldrich),
  1,1'-bis(diphenylphosphino)ferrocene (Fluka)
  tris(dibenzylideneacetone)dipalladium(0) (Acros),
  tri-o-tolylphosphine (Aldrich),
  1,4-bis(diphenylphosphino)butane (Aldrich)
  1,3,-bis(diphenylphosphino)propane (Acros),
  palladium acetate (Acros),
  tris(2-furyl)phosphine (Aldrich),
  tris(pentafluorophenyl)phosphine (Aldrich),
  triphenylarsenic (Acros),
  triphenylantimony (Acros),
  triphenylphosphine (Acros).

All the mineral reagents used were of analytical grade.

Protocols

Couplings With Tin Derivatives

3-Chloro-4-(pyrid-3-yl)-1,2,5-thiadiazole 0.4 g (0.0011 mol) of tributyl(3-pyridyl)stannane and 0.086 g (7.45×10$^{-5}$ mol) of tetrakis(triphenylphosphine) palladium(0) were added to a solution of 0.16 g (0.001 mol) of 3,4-dichloro-1,2,5-thiadiazole in 2 mL of toluene under argon and heated at reflux. After 2 h, 0.052 g (4.5×10$^{-5}$ mol) of tetrakis(triphenylphosphine) palladium(0) were added. After 24 h of reflux (quantitative HPLC: 38% of product formed, all the stannane was consumed), the reaction medium was diluted with 5 mL of ethyl acetate and vigorously stirred with 5 mL of a 1M aqueous solution of KF for 2 h. After filtration through celite, the aqueous phase was re-extracted with ethyl acetate, the combined organic phases were dried over magnesium sulfate and concentrated. The unprocessed oil was dissolved in 5 mL of cyclohexane and 5 mL of 1N HCl.

The aqueous phase was alkalinized and subsequently contained all the pyridine derivatives. The aqueous solution was saturated with sodium bicarbonate, extracted with ethyl acetate, dried over magnesium sulfate and concentrated. The product was purified by chromatography on silica gel (eluant: cyclohexane followed by cyclohexane/ethyl acetate 95/5–90/10). 3-chloro-4-(pyrid-3-yl)-1,2,5-thiadiazole was obtained in the form of a colorless oil which crystallized slowly (melting point 45° C., literature 48–49° C.).

3-Chloro-4-(pyrid-3-yl)-1,2,5-thiadiazole

To a solution of 3,4-dichloro-1,2,5-thiadiazole (0.31 g, 2mmol) and tributyl-(3-pyridyl)stannane (purchased from Maybridge) (0.74 g, 2 mmol) in dioxane (4 ml) under nitrogen is added tetrakis (triphenylphospine) palladium (0) (0.23 g, 0.2 mmol). The resulting yellow solution is refluxed under nitrogen for 20 hours.

The reaction mixture is concentrated under vacuum to afford an oil which is purified by flash chromatography on silica gel (50 g) eluting with cyclohexane and then with cyclohexane/ethyl acetate(95/5 to 90/10) to afford 0.27 g 968% [41.5% w/w by quantitative HPLC], effective yield= 28%, lot n° 97–114684)) of crude 3-chloro-4-(pyrid-3-yl)-1,2,5-thiadiazole as a colorless oil which crystallize on standing. Washing with n-heptane affords a white solid (m.p. 45° C.; m.p. 48–49° C. from n-heptane).

3-Chloro-4-(pyrid-3-yl)-1,2,5-thiadiazole

To a solution of 3-chloro-4-iodo-1,2,5-thiadiazole (62 mg, 0.25 mmol) in toluene (1 ml) under nitrogen is added tributyl-(3-pyridyl)stannane (92 mg, 0.25 mmol) and Pd$_2$dba$_3$ (5.7 mg, 5%mol). The resulting mixture is heated to reflux for 2 hours. A 76% yield was measured by quantitative HPLC, TLC (Hexane8/EtOAc2): only product. Similar results were obtained with 2% of Pd$_2$(dba)$_3$ as catalyst as well with Pd(CH$_3$CN)$_2$Cl$_2$ or Pd(OAc)$_2$.

3-Chloro-4-phenyl-1,2,5-thiadiazole 1.9 g (0.00517 mol) of tributylphenyl stannane and 0.29 g (0.00025 mol) of tetrakis (triphenylphosphine)palladium (0) were added to a solution of 0.775 g (0.005 mol) of 3,4-dichloro-1,2,5-thiadiazole in 10 mL of toluene under nitrogen and heated at reflux. After 8 h, 0.145 g (1.25×10$^{-4}$ mol) of tetrakis(triphenylphosphine)palladium(0) were added. After 24 h of reflux, 48% of product formed by quantitative HPLC (versus a reference prepared as reported by L. Weinstock et al., J. Org. Chem., vol. 32, p 2823 (1967)).

3-Chloro-4-(thiophen-2-yl)-1,2,5-thiadiazole 0.92 g (0.00246 mol) of 2-(tributylstannyl)thiophene and 0.12 g (0.0001 mol) of tetrakis(triphenylphosphine) palladium(0) were added to a solution of 0.33 g (0.00213 mol) of 3,4-dichloro-1,2,5-thiadiazole in 4 mL of toluene under nitrogen and heated at reflux. After 3 and 6 h respectively, 0.04 g (2 times 2.5×10$^{-5}$ mol) of tetrakis (triphenylphosphine)palladium(0) were added. After 24 h of reflux (quantitative HPLC: 54% of product formed, all the stannane was consumed), the reaction medium was diluted with 5 mL of ethyl acetate and vigorously stirred with 10 mL of a 1M aqueous solution of KF for 2 h. After filtration through celite, the aqueous phase was re-extracted with ethyl acetate, the combined organic phases were dried over magnesium sulfate and concentrated.

The product consists of 0.77 g of a black oil which was triturated in a hexane/ethyl acetate mixture (97/3). The precipitate, consisting primarily of triphenylphosphine sulfide was eliminated and the supernatant was purified by chromatography on silica gel (eluant: n-hexane) to produce 0.3 g of an ochre solid. After crystallization in pentane, the product consisted of 0.2 g (47%) of pure 3-chloro-4-(thiophen-2-yl)-1,2,5-thiadiazole (melting point range 45–47° C.). An analytical sample was prepared by further crystallization from methanol (m.p. 54–55° C.).

3-Chloro-4-(furan-2-yl)-1,2,5-thiadiazole 0.85 g (0.00238 mol) of 2-(tributylstannyl)furan and 0.12 g (0.0001 mol) of tetrakis(triphenylphosphine)palladium(0) were added to a solution of 0.33 g (0.00213 mol) of 3,4-dichloro-1,2,5-thiadiazole in 4 mL of toluene under nitrogen and heated at reflux. After 3 and 6 h respectively, 0.04 g (2 times $3.5 \times 10^{-5}$ mol) of tetrakis (triphenylphosphine)palladium(0) were added. After 24 h of reflux (quantitative HPLC: 60% of product formed, all the stannane was consumed), the reaction medium was diluted with 5 mL of ethyl acetate and vigorously stirred with 10 mL of a 1M aqueous solution of KF for 2 h. After filtration through celite, the aqueous phase was re-extracted with ethyl acetate, the combined organic phases were dried over magnesium sulfate and concentrated.

The product consisted of 0.86 g of a black oil which was triturated in a hexane/ethyl acetate mixture (97/3). The precipitate which consists primarily of triphenylphosphine sulfide was eliminated and the supernatant was purified by chromatography on silica gel (eluant: n-hexane then n-hexane/ethyl acetate 99/1) to produce 0.2 g (51%) of a solid. After crystallization in pentane, the product consisted of 0.14 g (36%) of pure 3-chloro-4-(furan-2-yl)-1,2,5-thiadiazole (melting point 46° C.).

3-Chloro-4-vinyl-1,2,5-thiadiazole 3.17 g (0.010 mol) of tributyl(vinyl)stannane and 0.56 g (0.0005 mol) of tetrakis(triphenylphosphine)palladium(0) were added to a solution of 1.55 g (0.010) mol of 3,4-dichloro-1,2,5-thiadiazole in 10 mL of toluene under nitrogen and heated at reflux. After 8 h, 0.28 g (0.00025 mol) of tetrakis(triphenylphosphine) palladium(0) were added. After 24 h of reflux (quantitative HPLC: 35% of product formed), the reaction medium was diluted with 10 mL of ethyl acetate and vigorously stirred with 15 mL of a 1 M aqueous solution of KF for 2 h. After filtration through celite, the aqueous phase was re-extracted with ethyl acetate, the combined organic phases were dried over magnesium sulfate and concentrated.

A black oil was obtained, which was triturated in a hexane/ethyl acetate mixture (97/3). The precipitate which consisted primarily of triphenylphosphine sulfide was eliminated, and the supernatant was purified by chromatography on silica gel (eluant: n-pentane) to produce 0.45 g (31%) of 3-chloro-4-vinyl-1,2,5-thiadiazole in the form of a colorless oil.

3-Chloro-4-(1-ethoxyvinyl)-1,2,5-thiadiazole 1.805 g (0.005 mol) of 1-(ethoxyvinyl)tributylstannane and 0.26 g (0.000225 mol) of tetrakis(triphenylphosphine) palladium(0) were added to a solution of 0.775 g (0.005 mol) of 3,4-dichloro-1,2,5-thiadiazole in 6 mL of toluene under nitrogen and heated at reflux. After 8h, 0.28 g (0.00025 mol) of tetrakis(triphenyl-phosphine)palladium(0) were added. After 24 h of reflux (quantitative HPLC: 55% of product formed), the reaction medium was diluted with 10 mL of ethyl acetate and vigorously stirred with 15 mL of a 1M aqueous solution of KF for 1 h. After filtration through celite, the aqueous phase was re-extracted with ethyl acetate, the combined organic phases were dried over magnesium sulfate and concentrated.

A black oil was obtained which was triturated in a hexane/ethyl acetate mixture (97/3). The precipitate which consisted primarily of triphenylphosphine sulfide was eliminated, and the supernatant was purified by chromatography on silica gel (eluant: n-pentane/diethyl ether 99/1) to produce 0.45 g (42%) of 3-chloro-4-(1-ethoxyvinyl)-1,2,5-thiadiazole in the form of a colorless oil.

3-Chloro-4-phenylethynyl-1,2,5-thiadiazole 2 g (0.005 mol) of tributyl(phenylethynyl)stannane and 0.23 g (0.0002 mol) of tetrakis(triphenylphosphine) palladium(0) were added to a solution of 0.62 g (0.004 mol) of 3,4-dichloro-1,2,5-thiadiazole in 8 mL of toluene under nitrogen and heated at reflux. After 4 and 24 h respectively, 0.115 g (0.0001 mol 2 times) of tetrakis(triphenylphosphine) palladium(0) was added. After 30 h of reflux (quantitative HPLC: 38% of product formed), the reaction medium was diluted with 10 mL of ethyl acetate and vigorously stirred with 15 mL of a 1 M aqueous solution of KF for 2 h. After filtration through celite, the aqueous phase was re-extracted with ethyl acetate, the combined organic phases were dried over magnesium sulfate and concentrated.

The product consisted of 2.83 g of a black oil which was triturated in a hexane/ethyl acetate mixture (97/3). The precipitate which consisted primarily of triphenylphosphine sulfide was eliminated, and the supernatant was purified by chromatography on silica gel (eluant: n-hexane) to produce 0.34 g (38.5% of an oil which crystallized slowly. After crystallization in hexane, the product consisted of 0.25 g (28.5%) of pure 3-chloro-4-phenylethynyl-1,2,5-thiadiazole (melting point 57° C.).

3-Chloro-4-allyl-1,2,5-thiadiazole 1.75 g (0.005 mol) of allyl(tributyl)stannane and 0.23 g (0.0002 mol) of tetrakis(triphenylphosphine)palladium(0) were added to a solution of 0.62 g (0.004 mol) of 3,4-dichloro-1,2,5-thiadiazole in 6 mL of toluene under nitrogen and heated at reflux. After 4 and 24 h respectively, 0.115 g (0.0001 mol 2 times) of tetrakis(triphenyl phosphine) palladium(0) was added. After 30 h of reflux (quantitative HPLC: 60% of product formed), the reaction medium was diluted with 10 mL of ethyl acetate and vigorously stirred with 15 mL of a 1M aqueous solution of KF for 2 h. After filtration through celite, the aqueous phase was re-extracted with ethyl acetate, the combined organic phases were dried over magnesium sulfate and concentrated.

The product consisted of 1.6 g of a black oil which was triturated in a hexane/ethyl acetate mixture (97/3). The precipitate which primarily consisted of triphenylphosphine sulfide was eliminated, and the supernatant was purified with chromatography on silica gel (eluant: n-hexane) to produce 0.2 g (31%) of 3-chloro-4-allyl-1,2,5-thiadiazole in the form of a colorless oil.

Couplings with Boron Derivatives

3-Chloro-4-phenyl-1,2,5-thiadiazole 0.35 g (0.006 mol) of KF, 0.245 g (0.002 mol) of phenylboric acid and 0.115 g (0.0001 mol) of tetrakis (triphenylphosphine)palladium(0) were added to a solution of 0.31 g (0.002 mol) of 3,4-dichloro-1,2,5-thiadiazole to a biphasic mixture of 5 mL of toluene and 5 mL of water under nitrogen and heated at reflux with vigorous stirring for 48 h. The organic phase was decanted and the aqueous phase was re-extracted with diethyl ether. The combined organic phases were dried over magnesium sulfate and concentrated.

The oily residue was purified by chromatography on silica gel (eluant: cyclohexane/diethyl ether 100/0 to 98/2) to produce 0.22 g (56%) of 3-chloro-4-phenyl-1,2,5-thiadiazole in the form of a colorless oil, which crystallizes on standing (m.p. 33° C.).

3-Chloro-4-(pyrid-3-yl)-1,2,5-thiadiazole 2 mL of a 1M aqueous solution of $K_2CO_3$ (0.002 mol), 0.147 g (0.001 mol) of diethyl(3-pyridyl)borane and 0.057 g (0.00005 mol) of tetrakis(triphenylphosphine)palladium(0) were added to a solution of 0.155 g (0.001 mol) of 3,4-dichloro-1,2,5-thiadiazole in 4 mL of toluene under nitrogen and heated at reflux with vigorous stirring for 24 h. The organic phase was decanted and the aqueous phase was re-extracted with diethyl ether. The combined organic phases were dried over magnesium sulfate and concentrated.

The oily residue was purified by chromatography on silica gel (eluant: cyclohexane/ethyl acetate 80/20) to produce 0.035 g (18%) of 3-chloro-4-(pyrid-3-yl)-1,2,5-thiadiazole in the form of a colorless oil which crystallizes slowly (melting point: 45° C.).

From 3-Bromo-4-chloro-1,2,5-thiadiazole.

To a mixture of 3-bromo-4-chloro-1,2,5-thiadiazole (0.2 g, 1 mmol), phenylboronic acid (0.135 g, 1.1 mol) in toluene (5 ml) is added a 1M aqueous solution of KF (3 cc, 3 mmol) and tetrakis(triphenylphosphine)palladium(0) (0.055 g, 0.05 mmol, 5%mol) and the biphasic mixture is refluxed with vigorous stirring for 26 hours. The organic layer is decanted off and the aqueous layer is extracted with toluene (2×10 ml). After drying over magnesium sulfate and concentration under vacuum, the oily material is purified by flash chromatography on silica gel eluting with hexane/ethyl acetate (99/1) to afford 0.18 g (95%) of 3-chloro-4-phenyl-1,2,5-thiadiazole as a colorless oil, which crystallizes on standing (melting point 33° C.).

From 3-Chloro-4-iodo-1,2,5-thiadiazole.

The experiment was repeated using 3-chloro-4-iodo-1,2,5-thiadiazole.

Preparation of 3-Chloro-4-halo-1,2,5-thiadiazoles

Synthesis of 3-Bromo-4-chloro-1,2,5-thiadiazole.

To a solution of $CuBr_2$ (53 g, 0.2385 mol) in anhydrous acetonitrile (500 ml) under nitrogen is added tert-butylnitrite (34 g, 0.3 mol). The resulting mixture is heated to 65–70° C. and a solution of 3-chloro-4-amino-1,2,5-thiadiazole (27 g, 0.2 mol) in anhydrous acetonitrile (300 ml) is added dropwise. Heating is maintained for 30 minutes after the end of the addition. After cooling to room temperature, water (400 ml) is added and acetonitrile is distilled off under vacuum. The resulting oily material is extracted with cyclohexane (2×400 ml). The combined organic layers are dried over $MgSO_4$ and concentrated to a mass of 30 g (75%). Distillation under reduced pressure affords 27.6 g (70%) of pure 3-bromo-4-chloro-1,2,5-thiadiazole (b.p.: 58° C./5 mbar).

Synthesis of 3-Chloro-4-iodo-1,2,5-thiadiazole.

To a suspension of CuI (22.83 g, 0.12 mol) in anhydrous acetonitrile (200 ml) under nitrogen is added tert-butylnitrite (15 g, 0.146 mol). The resulting mixture is heated to 60° C. and a solution of 3-chloro-4-amino-1,2,5-thiadiazole (13.45 g, 0.1 mol) in anhydrous acetonitrile (200 ml) is added dropwise within 30 minutes. Heating is maintained for 30 minutes after the end of the addition. After cooling to room temperature, water (1000 ml) is added and acetonitrile is distilled off under vacuum. The resulting oily material is extracted with cyclohexane (2×500 ml). The combined organic layers are washed with water (2×200 ml), dried over $MgSO_4$ and concentrated to a mass of 15 g. Distillation under reduced pressure affords 10 g (41%) of pure 3-iodo-4-chloro-1,2,5-thiadiazole (b.p.: 50–51° C./0.2mbar).

Bibliography

1 O. Hinsberg, Chem. Ber., 22, 2895 (1889)
2 L. B. Crast, Jr., U.S. Pat. No. 3,322,749 (1967)
3 a) R. R. Crenshaw & A. A. Algieri, Ger. Pat. 3 033 169 (1981)
   b) W. Lumma, et al., J. Med. Chem, et al. 25, 207 (1982)
   c) A. A. Algieri, et al., J. Med. Chem., 25, 210 (1982)
4 a) B. K. Wasson, et al., J. Med. Chem., 15, 651 (1972)
   b) L. M. Weinstock, et al., J. Org. Chem., 41, 3121 (1976)
5 a) P. H. Olesen, et al., Chirality, 9, 739–749 (1997)
   b) J. S. Ward, et al., J. Med. Chem., 41, 379–392 (1998)
6 Y. Hanasaki, et al., J. Med. Chem., 38, 2038–2040 (1995)
7 a) H. J. Knops, et al., Ger. Pat. 2 852 869 (1980)
   b) C. A. Wilson & C. E. Mixan, U.S. Pat. No. 4,075,205 (1978)
8 a) J Rokach & G. W. Reader, U.S. Pat. No. 4,094,986 (1978)
   b) G. K. Kohn & M. S. Singer, U.S. Pat. No. 3,854,000 (1974)
   c) J. Rokach, et al., U.S. Pat. No. 4,127,584 (1978)
9 a) R. H. Schieferstein & K. Pilgram, J. Agric. Food. Chem., 23, 393 (1975)
   b) K. D. Kearney, Eur. Pat. Appl. 0 414 511 (1990)
10 J. J. van Daelen & J. Daams, Naturwissenschaften, 57, 395 (1970)
11 S. T. D. Gough, U.S. Pat. No. 3,819,354 (1974)
12 M. Carmack & L. M. Weinstock, U.S. Pat. No. 3,066,147 (1962)
13 H. D. Brown & L. H. Sarett, U.S. Pat. No. 3,055,907 (1962)
   J. F. Engels & J. M. Puglis, U.S. Pat. No. 4,555,521 (1985)
14 P. E. Cassidy & N. C. Fawcett, J. Macromol. Sci., Rev. Macromol. Chem., C17, 209(1979)
15 L. M. Weinstock, et al., J. Org. Chem., 32, 2823 (1967)
16 Y. Hanasaki, Jap. Pat. 05 163 257 (1993)
17 S. C. Yoon, et al., J. Chem. Soc., Perkin Trans. 1, 109 (1998)
18 M. Becke-Goehring, Inorg. Synth., 6, 123 (1960)
   M. Villena-Blanco & W. L. Jolly, Inorg. Synth., 9, 98 (1967)
19 K. Tamao, et al., J. Amer, Chem. Soc., 94, 4374 (1972)
   M. Kumada, Pure & Appl. Chem., 52, 669–679 (1980)
20 R. J. P. Corriu & J. P. Masse, J. Chem. Soc., Chem. Commun., 144 (1972)
21 M. Yamamura, et al., J. Organometal. Chem., 91, C39 (1975)
22 E. Negishi, Pure & Appl. Chem., 53, 2333–2356 (1981)
23 S. Murahashi, et al., J. Org. Chem. , 44, 2408 (1979)
24 N. J. A. Alexakis & J. F. Normant, Tetrahedron Lett., 22, 959 (1981)
25 a) Y. Hatanaka & T. Hiyama, J. Org. Chem., 53, 918 (1988)
   b) Y. Hatanaka & T. Hilyama, Synlett, 845 (1991)
26 J. K. Stille, Angew. Chem. Int. Ed. Engl., 25, 508–524 (1986)
27 a) N. Miyaura, et al., Synth. Commun., 11, 513–519 (1981)
   b) N. Miyaura & A. Suzuki, Chem. Rev., 95, 2457–2483 (1995)
   c) A. R. Martin & Y. Yang, Acta Chemical Scandinavica, 47, 221–230 (1993)
   d) A. Suzuki, Pure & Appl. Chem., 66, 213–222 (1994)
28 a) K. Undheim & T. Bennech, Heterocycles, 30, 1155–1193 (1990)
   b) N. M. Ali, et al., Tetrahedron, 48, 8117–8126 (1992)
   c) M. B. Mitchell & P. J. Wallbank, Tetrahedron Lett., 32, 2273–2276 (1991)
29 Y. Hanasaki, Heterocycles, 43, 2435 (1996)
30 A. P. Komin & M. Carmack, J. Het. Chem., 13, 13 (1976)

What is claimed is:

1. A compound of the formula:

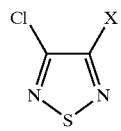

where X is I or Br.

* * * * *